US008784305B2

(12) United States Patent
DeSantis et al.

(10) Patent No.: US 8,784,305 B2
(45) Date of Patent: Jul. 22, 2014

(54) TISSUE RETRACTOR AND METHOD OF USE

(75) Inventors: Robert J. DeSantis, Redding, CT (US);
Gene Stellon, Burlington, CT (US);
Scott Depierro, Madison, CT (US)

(73) Assignee: Covidien LP, Mansfield, MA (US)

( * ) Notice: Subject to any disclaimer, the term of this patent is extended or adjusted under 35 U.S.C. 154(b) by 555 days.

(21) Appl. No.: 12/571,905

(22) Filed: Oct. 1, 2009

(65) Prior Publication Data

US 2010/0094094 A1 Apr. 15, 2010

Related U.S. Application Data

(60) Provisional application No. 61/104,102, filed on Oct. 9, 2008.

(51) Int. Cl.
*A61B 1/32* (2006.01)
*A61B 17/02* (2006.01)
*A61B 17/04* (2006.01)
*A61B 17/06* (2006.01)
*A61B 17/062* (2006.01)

(52) U.S. Cl.
CPC ......... *A61B 17/0401* (2013.01); *A61B 17/0218* (2013.01); *A61B 2017/0472* (2013.01); *A61B 17/0469* (2013.01); *A61B 2017/0417* (2013.01); *A61B 2017/06176* (2013.01); *A61B 1/32* (2013.01); *A61B 2017/06028* (2013.01); *A61B 17/062* (2013.01)
USPC .......................................... 600/217; 600/210

(58) Field of Classification Search
USPC .......... 600/201, 217; 606/144–146, 222–233, 606/139; 128/898
See application file for complete search history.

(56) References Cited

U.S. PATENT DOCUMENTS

| | | | | |
|---|---|---|---|---|
| 4,069,825 A * | 1/1978 | Akiyama | ....................... | 606/158 |
| 4,549,545 A * | 10/1985 | Levy | ............................. | 606/228 |
| 5,074,874 A * | 12/1991 | Yoon et al. | .................... | 606/224 |
| 5,269,783 A * | 12/1993 | Sander | .......................... | 606/148 |
| 5,337,736 A * | 8/1994 | Reddy | ............................ | 600/217 |
| 5,362,294 A * | 11/1994 | Seitzinger | ...................... | 600/37 |
| 5,374,268 A | 12/1994 | Sander | | |
| 5,383,904 A * | 1/1995 | Totakura et al. | ............... | 606/228 |
| 5,391,173 A | 2/1995 | Wilk | | |
| 5,425,747 A | 6/1995 | Brotz | | |
| 5,500,000 A | 3/1996 | Feagin et al. | | |
| 5,584,859 A | 12/1996 | Brotz | | |
| 5,593,424 A * | 1/1997 | Northrup III | ................. | 606/232 |
| 5,626,590 A | 5/1997 | Wilk | | |
| 5,782,864 A * | 7/1998 | Lizardi | ........................ | 606/232 |
| 5,931,855 A | 8/1999 | Buncke | | |
| 6,167,889 B1 * | 1/2001 | Benetti | ........................ | 128/898 |
| 6,383,199 B2 * | 5/2002 | Carter et al. | ................... | 606/148 |

(Continued)

OTHER PUBLICATIONS

Obstetrics and Gynecology 1992, 79; 143-147.*

*Primary Examiner* — Ellen C Hammond
*Assistant Examiner* — Jacqueline Johanas

(57) ABSTRACT

A method of retracting and/or manipulating tissue is provided. The method includes providing access to a body cavity, providing a retractor including a elongated body portion, a needle formed on a proximal end of the elongated body portion and an anchor means formed on a distal end of the elongated body portion, directing the needle of the retractor through a section of tissue to be retracted, drawing the retractor though the tissue until the anchor means engages the tissue, and pulling the body portion of the retractor to manipulate the tissue.

7 Claims, 16 Drawing Sheets

(56) References Cited

U.S. PATENT DOCUMENTS

| | | | |
|---|---|---|---|
| 6,454,783 B1* | 9/2002 | Piskun | 606/185 |
| 6,599,310 B2 | 7/2003 | Leung et al. | |
| 6,641,596 B1* | 11/2003 | Lizardi | 606/232 |
| 6,773,450 B2 | 8/2004 | Leung et al. | |
| 7,056,331 B2 | 6/2006 | Kaplan et al. | |
| 7,226,468 B2 | 6/2007 | Ruff | |
| 7,235,091 B2* | 6/2007 | Thornes | 606/232 |
| 7,371,253 B2 | 5/2008 | Leung et al. | |
| 7,601,164 B2 | 10/2009 | Wu | |
| 7,799,073 B2* | 9/2010 | Khalapyan | 623/2.37 |
| 7,837,612 B2* | 11/2010 | Gill et al. | 600/37 |
| 7,842,050 B2* | 11/2010 | Diduch et al. | 606/148 |
| 8,251,889 B2* | 8/2012 | Scott | 600/37 |
| 8,465,515 B2* | 6/2013 | Drew et al. | 606/204 |
| 2003/0014077 A1 | 1/2003 | Leung et al. | |
| 2003/0171778 A1* | 9/2003 | Lizardi | 606/232 |
| 2004/0060409 A1 | 4/2004 | Leung et al. | |
| 2004/0060410 A1 | 4/2004 | Leung et al. | |
| 2004/0088003 A1 | 5/2004 | Leung et al. | |
| 2004/0098053 A1* | 5/2004 | Tran | 606/232 |
| 2004/0153102 A1* | 8/2004 | Therin et al. | 606/144 |
| 2004/0236419 A1* | 11/2004 | Milo | 623/2.36 |
| 2005/0004576 A1 | 1/2005 | Benderev | |
| 2005/0033367 A1* | 2/2005 | Leung et al. | 606/232 |
| 2005/0177190 A1 | 8/2005 | Zamierowski | |
| 2005/0199249 A1 | 9/2005 | Karram | |
| 2005/0203344 A1* | 9/2005 | Orban et al. | 600/204 |
| 2005/0267531 A1 | 12/2005 | Ruff et al. | |
| 2006/0111734 A1 | 5/2006 | Kaplan et al. | |
| 2006/0111742 A1 | 5/2006 | Kaplan et al. | |
| 2006/0135994 A1 | 6/2006 | Ruff et al. | |
| 2006/0135995 A1 | 6/2006 | Ruff et al. | |
| 2006/0235447 A1 | 10/2006 | Walshe | |
| 2006/0258899 A1* | 11/2006 | Gill et al. | 600/37 |
| 2006/0264699 A1* | 11/2006 | Gertner | 600/37 |
| 2007/0005109 A1 | 1/2007 | Popadiuk et al. | |
| 2007/0005110 A1 | 1/2007 | Collier et al. | |
| 2007/0208377 A1 | 9/2007 | Kaplan et al. | |
| 2007/0224237 A1 | 9/2007 | Hwang et al. | |
| 2007/0233170 A1* | 10/2007 | Gertner | 606/192 |
| 2007/0265659 A1* | 11/2007 | Williamson | 606/224 |
| 2008/0004490 A1 | 1/2008 | Bosley et al. | |
| 2008/0027486 A1 | 1/2008 | Jones et al. | |
| 2008/0033488 A1* | 2/2008 | Catanese et al. | 606/232 |
| 2008/0058869 A1 | 3/2008 | Stopek et al. | |
| 2008/0077181 A1 | 3/2008 | Jones et al. | |
| 2008/0082113 A1* | 4/2008 | Bishop et al. | 606/151 |
| 2008/0082129 A1 | 4/2008 | Jones et al. | |
| 2008/0086170 A1 | 4/2008 | Jones et al. | |
| 2008/0109036 A1 | 5/2008 | Stopek et al. | |
| 2008/0195147 A1 | 8/2008 | Stopek | |
| 2008/0215072 A1* | 9/2008 | Kelly | 606/151 |
| 2008/0234731 A1* | 9/2008 | Leung et al. | 606/232 |
| 2008/0312688 A1 | 12/2008 | Nawrocki et al. | |
| 2009/0018577 A1 | 1/2009 | Leung et al. | |
| 2009/0043336 A1 | 2/2009 | Yuan et al. | |
| 2009/0062618 A1* | 3/2009 | Drew et al. | 600/204 |
| 2009/0082806 A1 | 3/2009 | West, Jr. et al. | |
| 2009/0171143 A1* | 7/2009 | Chu et al. | 600/37 |
| 2009/0248066 A1 | 10/2009 | Wilkie | |
| 2009/0250356 A1 | 10/2009 | Kirsch et al. | |
| 2010/0021516 A1* | 1/2010 | McKay | 424/422 |
| 2010/0114162 A1* | 5/2010 | Bojarski et al. | 606/228 |
| 2010/0228093 A1* | 9/2010 | Voegele et al. | 600/204 |
| 2011/0087067 A1* | 4/2011 | Rodrigues et al. | 600/37 |
| 2011/0087249 A1* | 4/2011 | Rodrigues et al. | 606/151 |
| 2012/0227748 A1* | 9/2012 | Sanders | 128/848 |

* cited by examiner

TISSUE RETRACTOR AND METHOD OF USE

CROSS-REFERENCE TO RELATED APPLICATIONS

This application claims the benefit of and priority to U.S. Provisional Patent Application No. 61/104,102, filed Oct. 9, 2008, the entire disclosure of which is incorporated by reference herein.

BACKGROUND

1. Technical Field

The present disclosure relates to single incision or laparoscopic surgery. More particularly, the present disclosure relates to tissue retractors for use during laparoscopic surgery.

2. Background of Related Art

Methods for performing single incision or laparoscopic surgical procedures are known and are becoming more widely used. Operating through a single incision or port permits a surgeon to perform an extensive array of procedures with minimal scarring and faster recovery time for a patient. Smaller, more precise instruments and other advances in medicine have brought about an increase in the number of procedures that may be performed laparoscopically. The reduced space in which a surgeon has to insert instruments within a patient limits the number of instruments that may be received in a patient at any given time.

When operating in the abdominal cavity, a surgeon may find the need to retract or move one or more organs or other tissue to better access a target site with the cavity. Conventional retractors tend to be long and rigid, and therefore, not suitable for laparoscopic use. Furthermore, inserting a conventional retractor through the incision or port may require a larger incision or port. When a port assembly is used, insertion of a conventional retractor through one of the ports of the assembly occupies that port for the duration of the procedure and eliminates the use of the port with another instrument.

Therefore, a continuing need exists for a tissue retractor and method of retracting tissue that is more suitable for use during laparoscopic procedures.

SUMMARY

Accordingly, method of retracting tissue is provided. The method includes the steps of providing laparoscopic access to a body cavity, providing a retractor including a elongated body portion, a needle formed on a proximal end of the elongated body portion and an anchor means formed on a distal end of the elongated body portion, directing the needle of the retractor through a section of tissue to be retracted, drawing the retractor though the tissue until the anchor means engages the tissue, and pulling the body portion of the retractor to manipulate the tissue. The method may further include the step of withdrawing the proximal end of the retractor from the body cavity. The method may also include the step of anchoring the proximal end of the retractor exterior of the body cavity. The anchor means may include a pledget.

The retractor of the provided method may be completely received within the body cavity of a patient, or instead the proximal end of the retractor may extend from the body cavity. The needle of the retractor may be directed through a wall of the body cavity or instead may be partially directed through the wall of the body cavity. The elongated body portion of the retractor may include multiple body portions. The elongated body portion of the retractor may include multiple needles. The anchor means may include proximally extending barbs.

Another method of retracting tissue is provided. The method includes the steps of providing laparoscopic access to a body cavity, providing a retractor including a elongated body portion and a needle formed on a proximal end, wherein the proximal end of the elongated body portion further includes barbs for engaging tissue, directing the needle of the retractor through a section of tissue to be retracted, drawing the retractor though the tissue until the barbs formed thereon engage the tissue, and pulling on a distal end of the retractor to set the barbs in the tissue. The distal end of the retractor may remain external of the body cavity. The distal end of the retractor may be anchored external of the body cavity. The method may further include the step of pulling on the distal end of the retractor to manipulate the tissue.

Still another method of retracting tissue is provided. The method includes the steps of providing laparoscopic access to a body cavity, providing a retractor including a elongated body portion including a needle and barbs formed on a first end and a support member having a first end integrally formed with a second end of the body portion, the support member including a fastener on a second end thereof for selectively securing the second end of the support member to the elongated body portion, placing the support member of the retractor around a section of tissue to be retracted, engaging the fastener formed on the second end of the support member to the elongated body portion of the retractor, directing the needle of the retractor through the skin of a patient, and drawing the needle though the tissue until the barbs formed thereon engage the skin. The fastener formed on the support member may be one of a hook and a clip. The support member may form a sling. The support member may be configured to support the tissue in a hammock-like manner.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Although the embodiments of the present disclosure will be described as relates to use in single incision or laparoscopic surgery, the aspects of the present disclosure may be modified for use in procedures other than those performed through a laparoscopic port. For example, the embodiments of the present disclosure may be modified for use in open surgery and endoluminally through a natural orifice.

Figure 1:
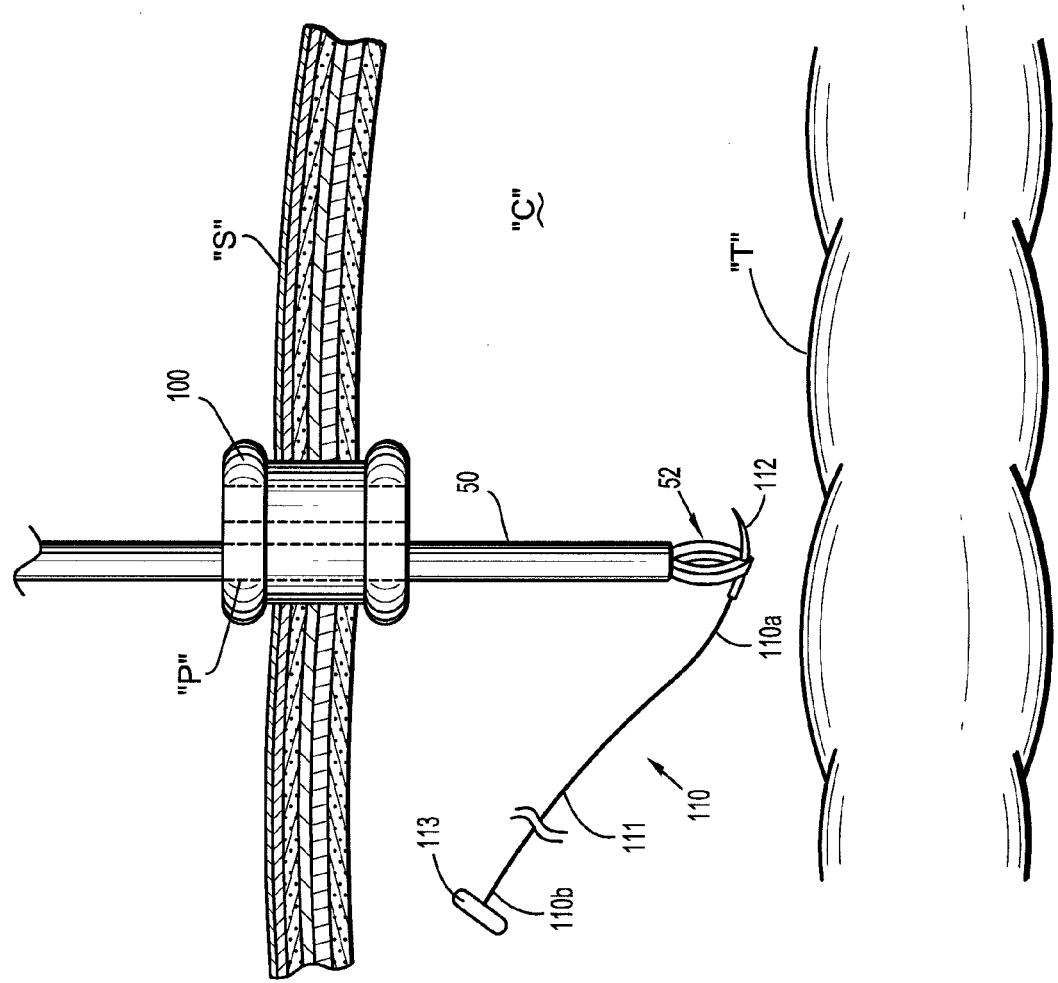
FIGS. 1-4 illustrate of a method of retracting tissue using an tissue retractor according to an embodiment of the present disclosure.

With reference now to FIGS. 1-4, a first method for retracting an organ is illustrated. Referring initially to FIG. 1, using known surgical techniques, a laparoscopic port 100 is inserted through skin "S" of a patient to access a body cavity "C". A tissue retractor 110 is then inserted through laparoscopic port 100 and is received within body cavity "C".

With reference still to FIG. 1, tissue retractor 110 includes a substantially elongated body portion 111 having a needle 112 on a proximal end 110a and a pledget 113 formed on a distal end 110b. Body portion 111 of retractor 110 may be formed from any known material, including absorbable and non-absorbable thread. Pledget 113 may be formed from plastic, polymer or other biocompatible material. Pledget 113 may be integrally formed with body portion 110. In an alternative embodiment, pledget 113 may instead be securely affixed to distal end 110b of retractor 110 using adhesive, glue, mechanical fasteners, welding or other suitable technique. In one embodiment, pledget 113 is composed of an absorbable material for use with an absorbable suture. In this manner, pledget 113 may remain with body cavity "C" following completion of a procedure.

Figure 2:
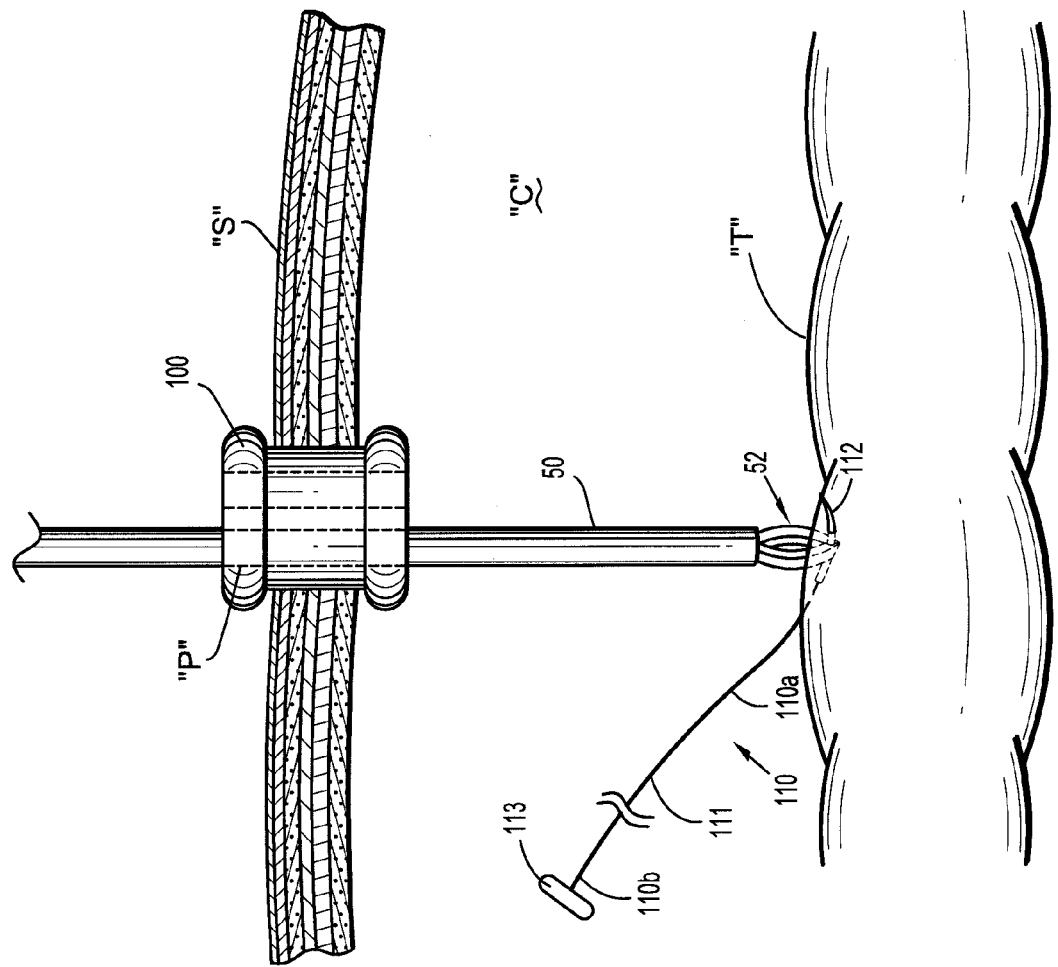

Still referring to FIG. 1, needle 112 of retractor 110 is first grasped within jaw members 52 of a laparoscopic instrument 50. Turning to FIG. 2, instrument 50 is then externally manipulated by a surgeon using known techniques to direct needle 112 of retractor 110 through a section of tissue "T" to be retracted. Although shown as a section of small/large intestine, tissue "T" may include any tissue or organ within the body. Once a proximal end of needle 112 is visible through tissue "T", needle 112 is released from within jaw members 52 and the exposed end of needle 112 is regrasped within jaw members 52.

Figure 3:
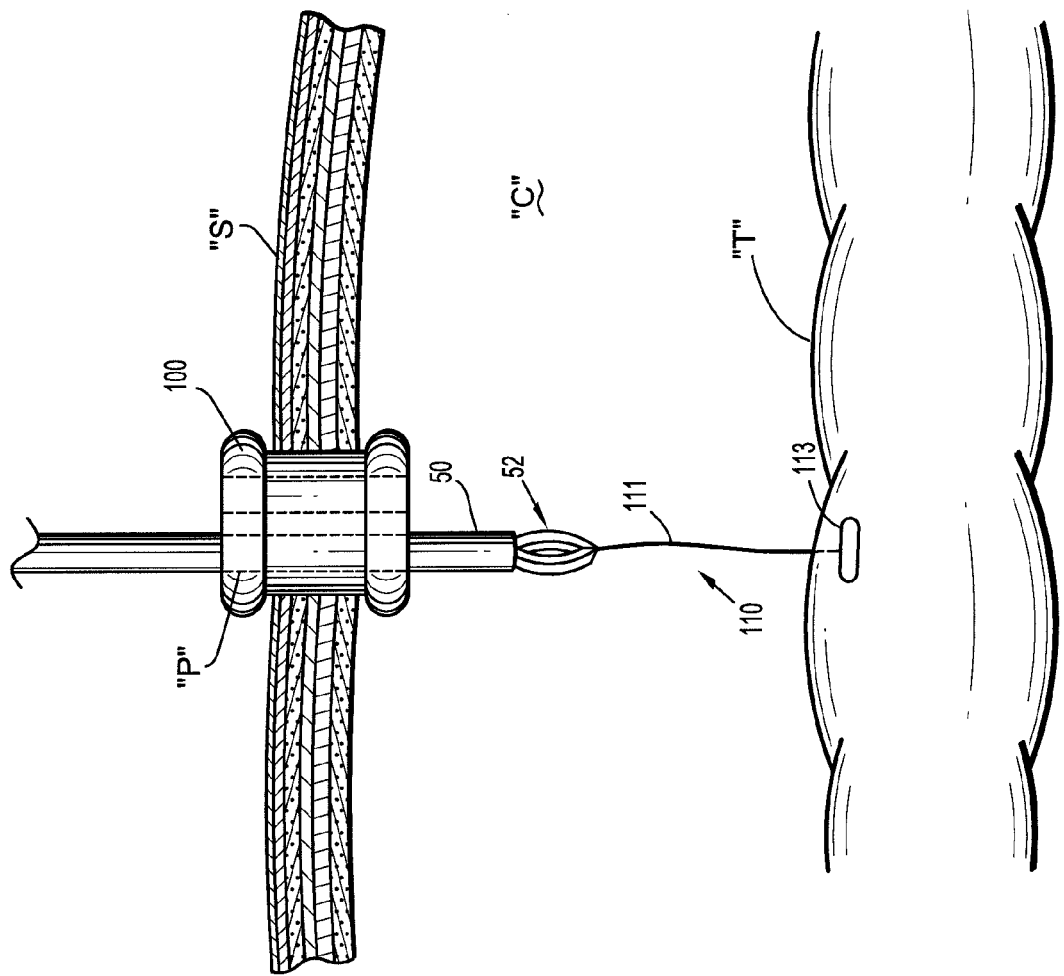

Turning to FIG. 3, as instrument 50 is pulled distally through laparoscopic port 100, retractor 110 is drawn through tissue "T" until pledget 113 formed on distal end 110b of retractor 110 engages tissue "T". Retractor 110 may need to be released and regrasped one or more times to draw body portion 111 through tissue "T" and to engage pledget 113. Once pledget 113 of retractor 110 has engaged tissue "T", any further manipulation of retractor 110 causes movement of tissue "T". For example, continued withdrawal of retractor 110 from laparoscopic port 100 causes retraction of tissue "T", in the direction of arrow "A" (FIG. 4)

Figure 4:
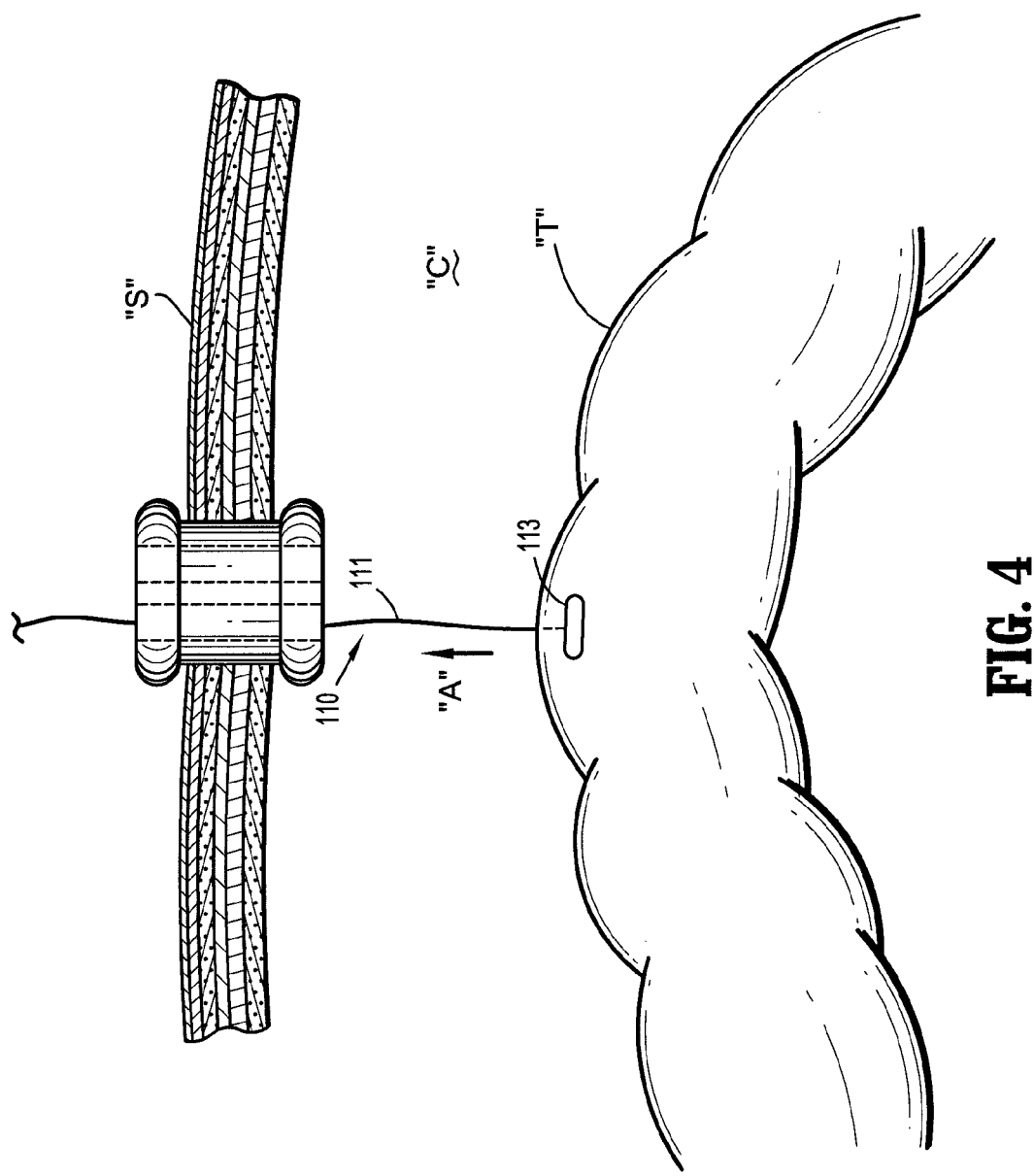

With reference now to FIG. 4, laparoscopic instrument 50 may be completely withdrawn from laparoscopic port 100 along with proximal end 110a of retractor 110. In this manner, proximal end 110a of retractor 110 is accessible to a surgeon. Alternatively, proximal end 110a of retractor 110 may be retained within body cavity "C" for further manipulation using instrument 50. In one embodiment, laparoscopic port 100 may include an anchor (not shown) on which proximal end 110a of retractor 110 may be tied. Alternatively, once received through passage "P" of laparoscopic port 100, proximal end 110a may be continually grasped by a surgeon for further manipulation of tissue "T", or instead, proximal end 110a may otherwise be selectively anchored outside of body cavity "C". By suspending tissue "T" within body cavity "C" from flexible retractor 110, tissue "T" may freely move within body cavity "C". Thus, if tissue "T" is incidentally contacted by an instrument (not shown) during a laparoscopic procedure, the trauma to tissue "T" from the contact is minimized. When retractor 110 is received through passageway "P" in laparoscopic port 100, there is sufficient room within passageway "P" for an additional instrument (not shown) to be inserted therethrough. In this manner, a single passageway of laparoscopic port 100 may be used for multiple purposes. In one embodiment, laparoscopic port 100 includes a groove or slot (not shown) extending along passageway "P" configured to receive retractor 110 such that other instruments (not shown) may be inserted through passageway "P" without engaging retractor 110.

Upon completion of a laparoscopic procedure, all, a portion or none of retractor 110 may removed from body cavity "C". When retractor 110 is removed from body cavity "C" a surgeon grasps pledget 113 and draws retractor 110 back through tissue "T". Needle 112 is separated from retractor 110 prior withdrawal to facilitate withdrawal of retractor 110. The surgeon may elect to cut retractor 110 along body portion 111 to limit the amount of retractor 110 that must be drawn through tissue "T". Once retractor 110 is no longer engaged with tissue "T", retractor 110, or the pieces that once formed retractor 110 are removed from body cavity "C" through laparoscopic port 100. In an alternative method, the portion of retractor 110 extending from laparoscopic port 100 is cut and the remaining portion of retractor 110 is left within body cavity "C" to be absorbed.

Figure 5:
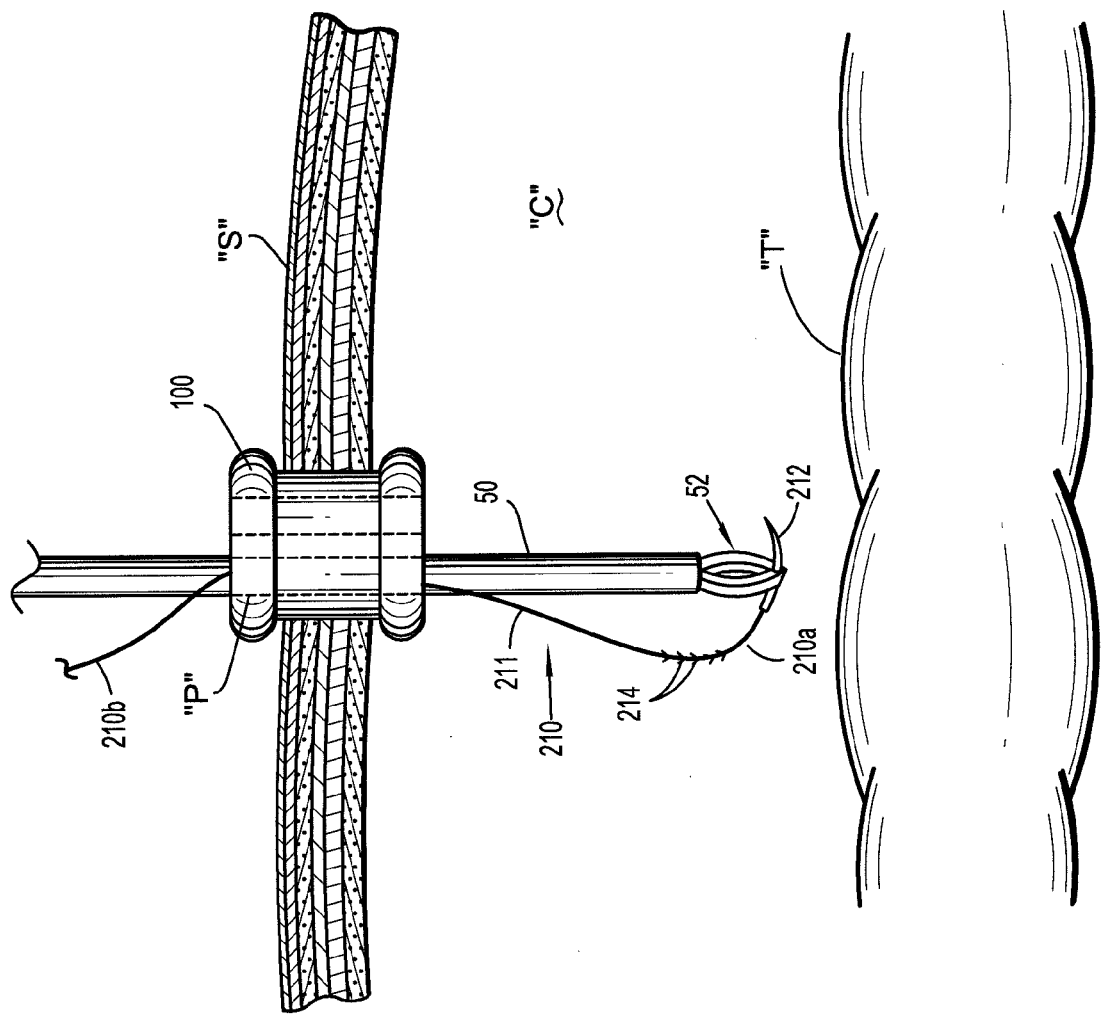
FIGS. 5-7 illustrate another method of retracting tissue using another tissue retractor according to the present disclosure.
Figure 6:
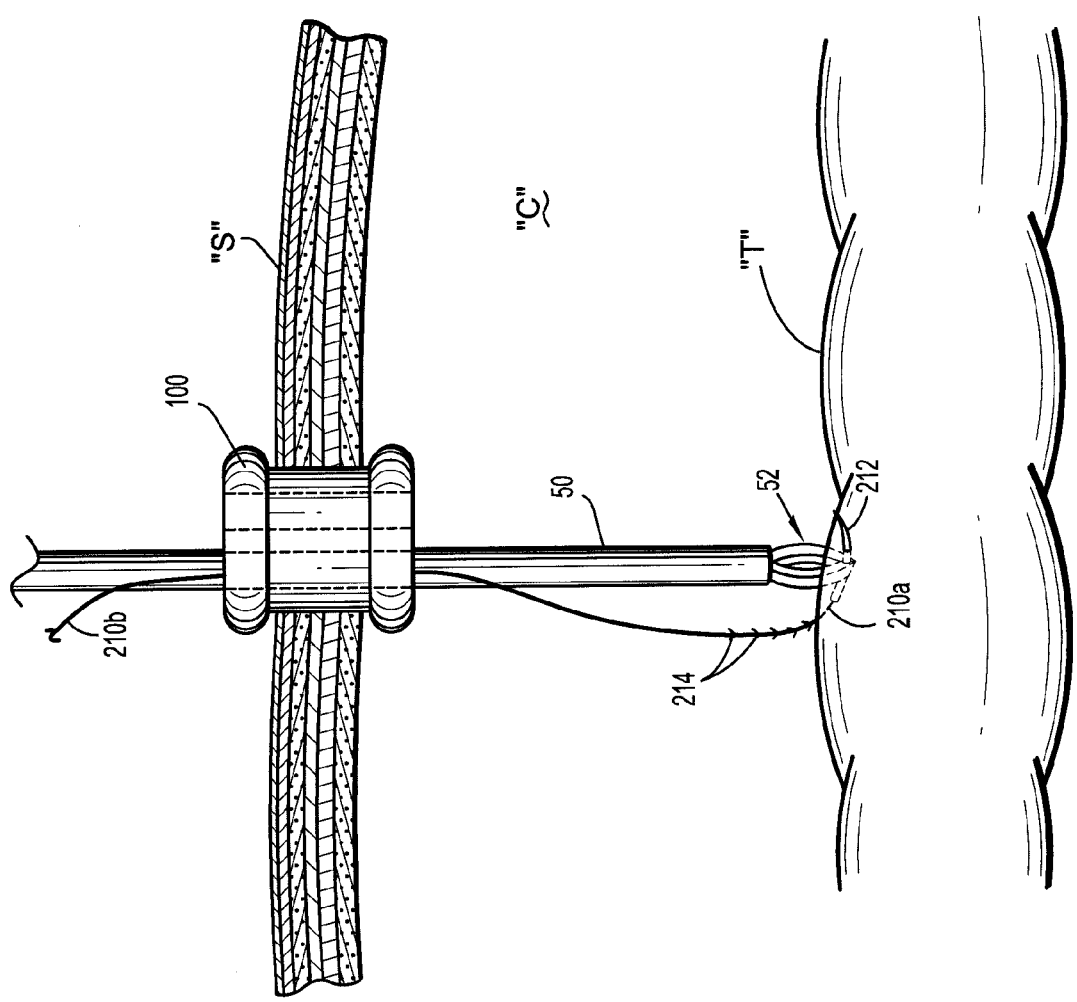
Figure 7:
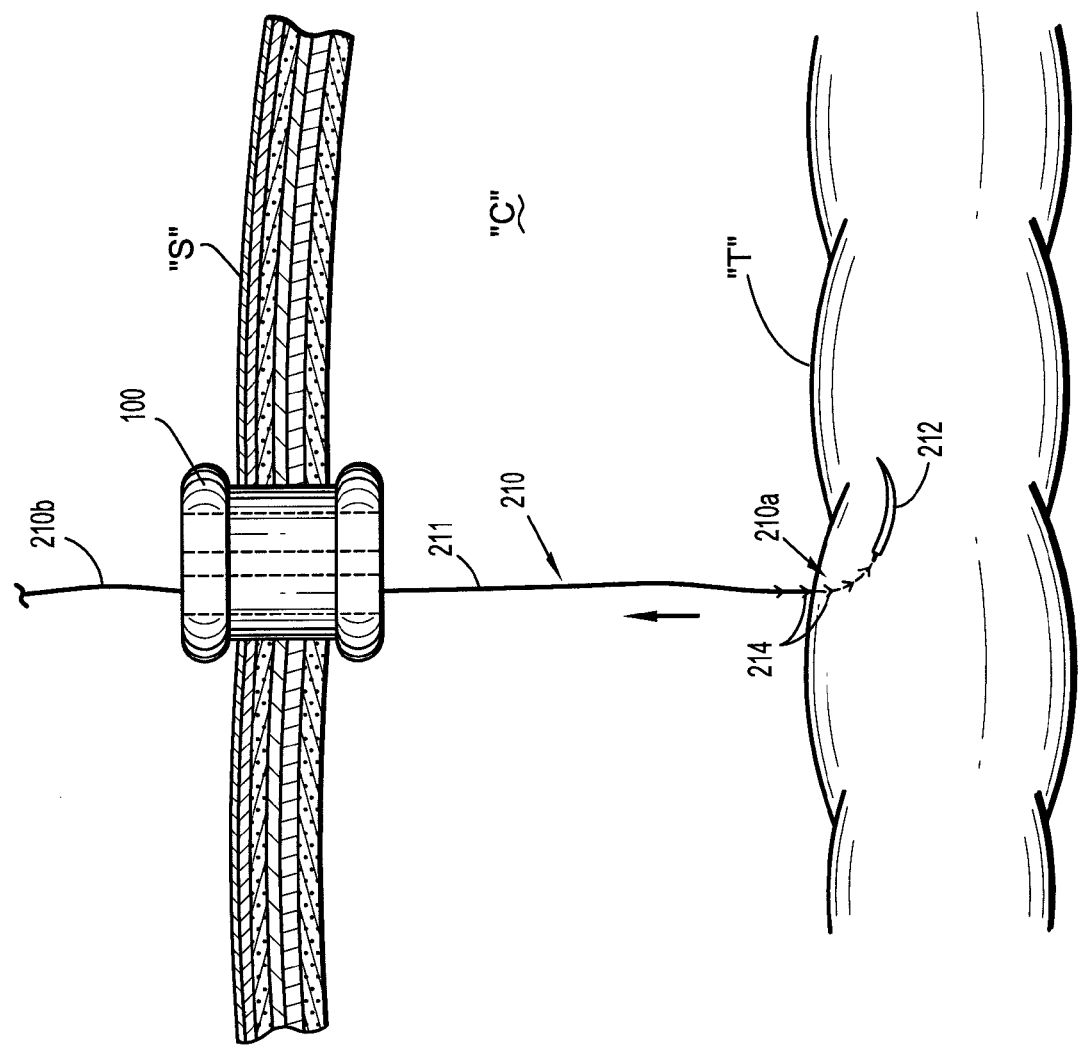

With reference now to FIGS. 5-7, an alternative method of retracting tissue "T" according to the present disclosure is illustrated. Referring initially to FIG. 5, laparoscopic port 100 is inserted through skin "S" to access body cavity "C". A needle 212 on a proximal end 210a of a tissue retractor 210 according to another embodiment of the present disclosure is grasped within jaws 52 of a laparoscopic instrument 50 and is received through passageway "P" formed in laparoscopic port 100. Tissue retractor 210 further includes a plurality of barbs 214 formed on proximal end 210a thereof distal of needle 212. During the procedure, a distal end 210b of retractor 210 remains outside of body cavity "C".

Turning to FIG. 6, instrument 50 is used to direct needle 212 through a section of tissue "T". Once a proximal end of needle 212 is visible through tissue "T", needle 212 is released from within jaw members 52 and the exposed end of needle 212 is regrasped within jaw members 52. Proximal end 210a of retractor 210 is then drawn through tissue "T" a sufficient length to engage barbs 214 formed on proximal end 210a. Once barbs 214 have engaged tissue "T", needle 212 is released from jaw members 52.

With reference now to FIG. 7, retraction of distal end 210b of retractor 210 through laparoscopic port 100 causes barbs 214 to bite into tissue "T", thereby engaging tissue "T" and permitting retraction thereof through external manipulation of retractor 210. As with the method of retraction described above, passageway "P" formed through laparoscopic port 100 may be used to receive an additional instrument (not shown).

Removal of retractor 210 from within body cavity "C" may be accomplished by grasping needle 212 and continuing to draw retractor 210 through tissue "T". To limit the amount of retractor 210 that must be drawn through tissue "T", retractor 210 may be cut anywhere along the length thereof distal of tissue "T".

Figure 8:
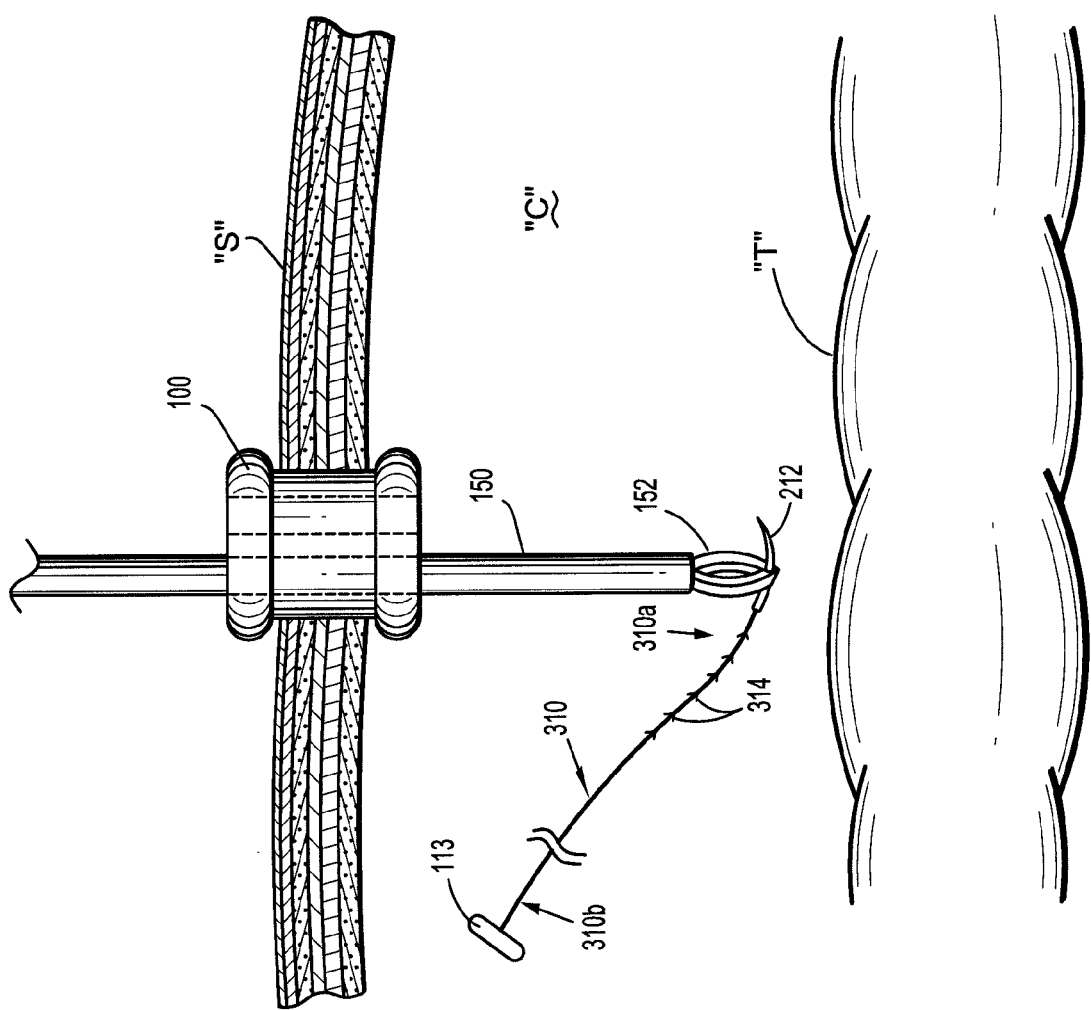
FIGS. 8-11 illustrate yet another method of retracting tissue using yet another tissue retractor according to the present disclosure.

Turning now to FIGS. 8-11, another method of retracting tissue "T" according to the present disclosure is illustrated. With reference initially to FIG. 8, laparoscopic port 100 is inserted through skin "S" and a tissue retractor 310 according to an alternative embodiment of the present disclosure is received within body cavity "C". Tissue retractor 310 includes a needle 312 formed on a proximal end 310a thereof and a pledget 313 formed on a distal end 310b thereof. In an alternative embodiment, distal end 310b of retractor 310 may include barbs (not shown) formed extending proximal towards needle 312. In this manner, the barbs formed on distal end 310b of retractor 310 would act as an end effector, thereby preventing retractor 310 from being pulled through tissue "T". Proximal end 310a of retractor 310 includes barbs 314. Needle 312 of retractor 310 is then received within jaw members 152 of laparoscopic instrument 150.

Figure 9:
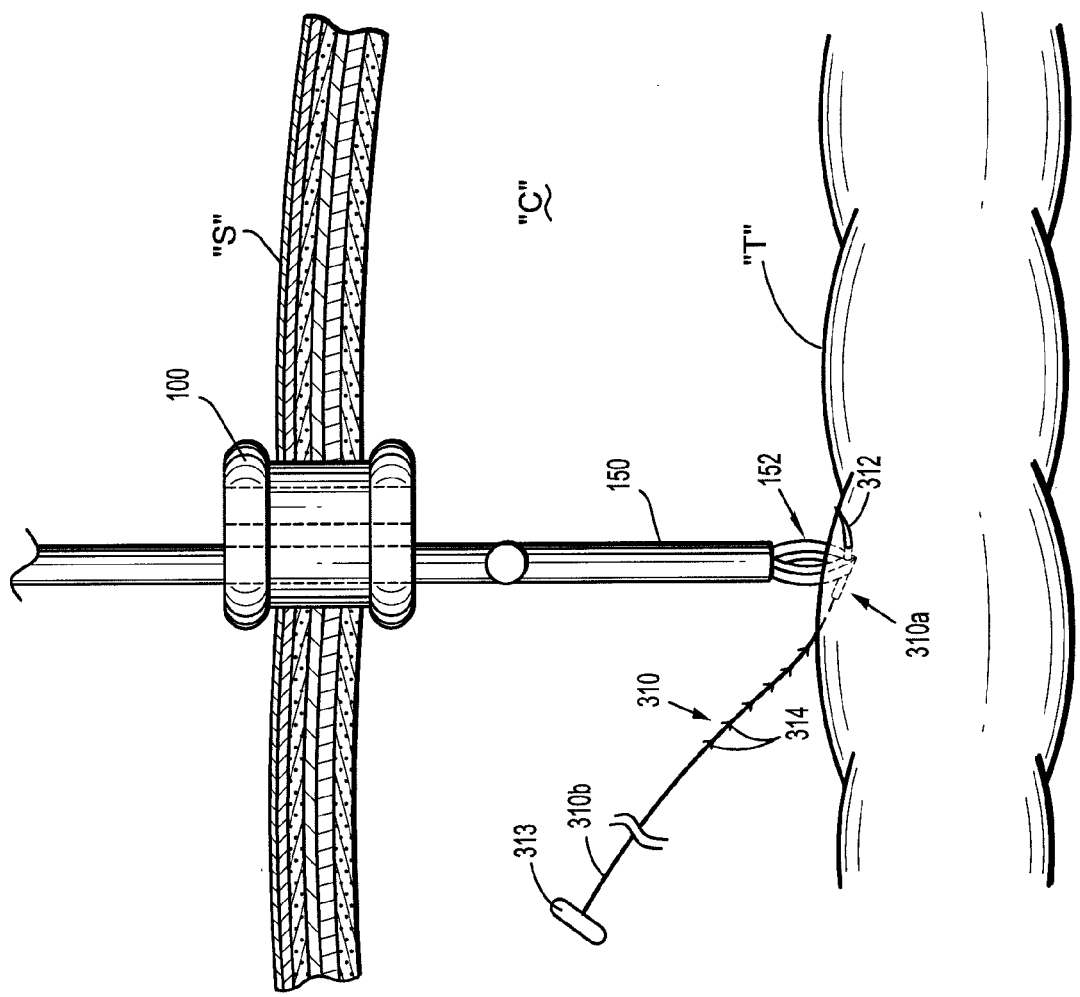

With reference now to FIG. 9, instrument 150 is then externally manipulated by a surgeon using known techniques to direct needle 312 of retractor 310 through a section of tissue "T" to be retracted. Once a proximal end of needle 312 is visible through tissue "T", needle 312 is released from within jaw members 152 and the exposed end of needle 312 is regrasped within jaw members 152. Retractor 310 is then drawn through tissue "T" until pledget 313 engages tissue "T". In an alternative embodiment, retractor 310 is drawn through tissue "T" until barbs (not shown) formed on distal end 310b engage tissue "T".

Figure 10:
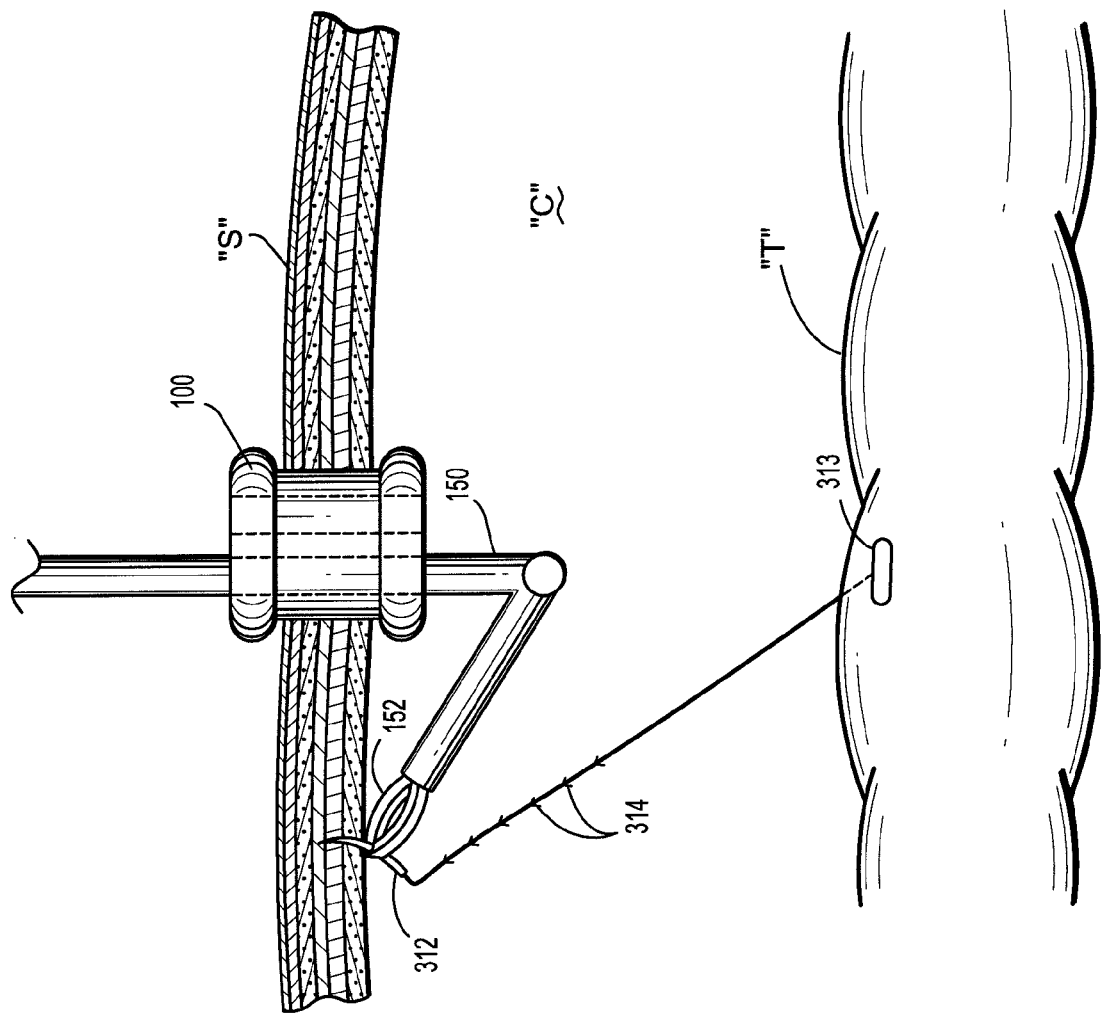
Figure 11:
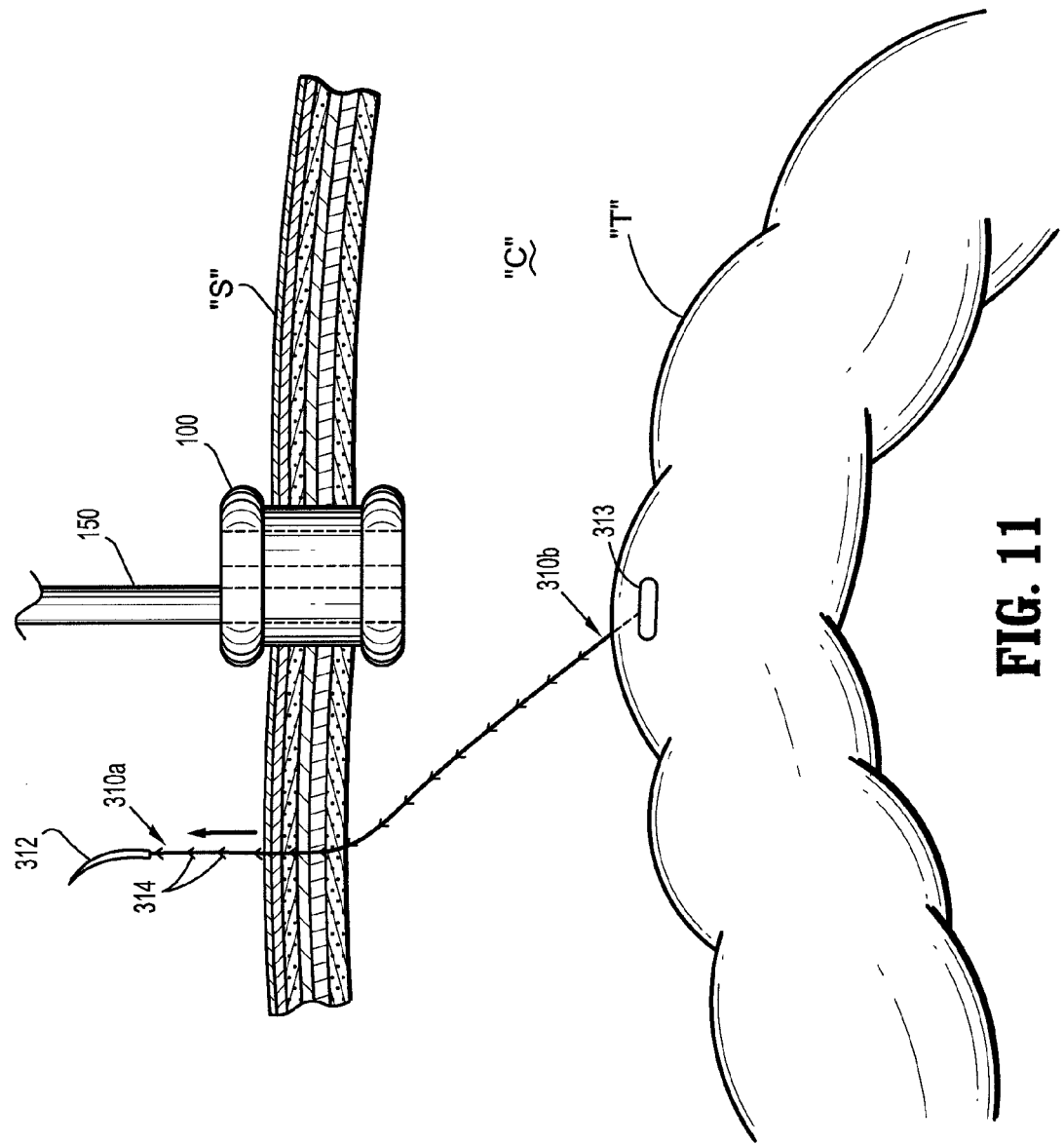

Turning to FIG. 10, laparoscopic instrument 152 is then manipulated to direct needle 312 of retractor 310 through skin "S". With reference to FIG. 11, once needle 312 is received through skin "S", a surgeon may grasp needle 312 external of body cavity "C" and continue to draw retractor 310 through skin "S". Barbs 314 formed along proximal end 310a of retractor 310 prevent retractor 310 from being drawn back through skin "S". Retractor 310 may be further drawn through skin "S" to further retract tissue "T".

Figure 12:
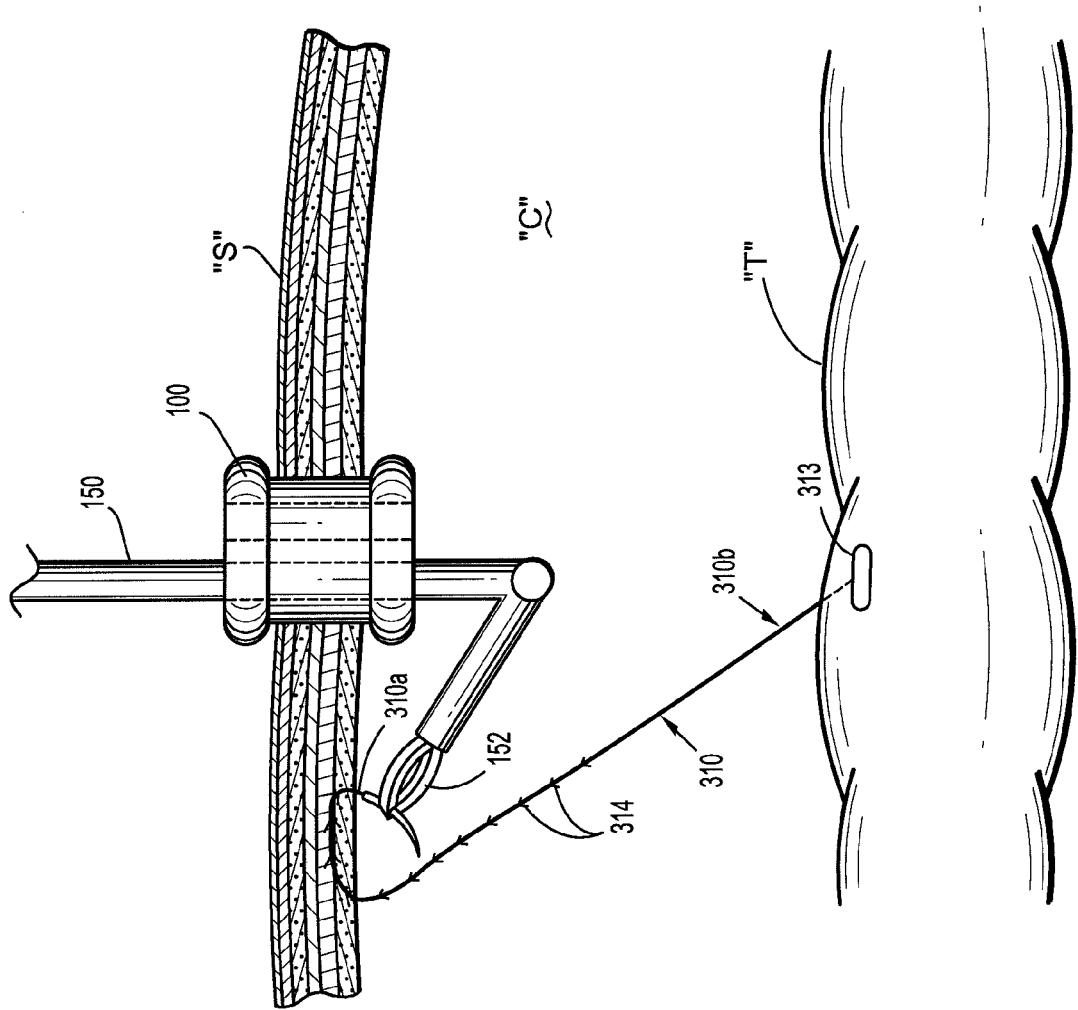
FIGS. 12 and 13 illustrate still another method of retracting tissue using the tissue retractor illustrated in FIGS. 8-11.
Figure 13:
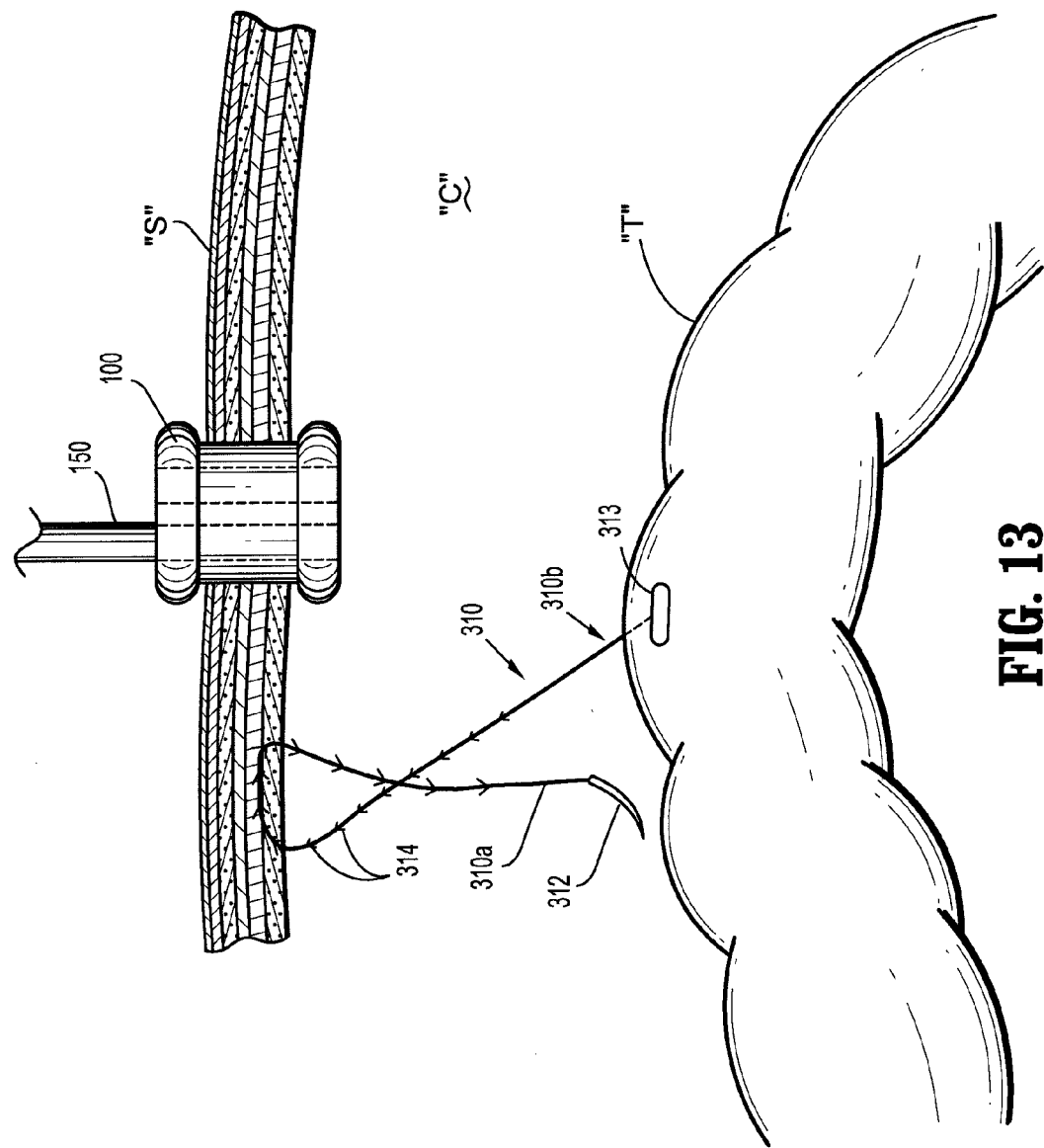

Alternatively, and with reference to FIGS. 12 and 13, needle 312 of retractor 310 may instead be directed through less than all the layers of skin "S" (FIG. 12). Once a proximal end of needle 312 is visible through skin "S", needle 312 is released from within jaw members 152 and the exposed end of needle 312 is regrasped within jaw members 152. Retractor 310 may then be drawn through the layers of skin "S" to retract tissue "T". Barbs 314 formed on proximal end 310a of retractor 310 prevent retractor 310 from being drawn back through the layers of skin "S".

To remove retractor 310 from body cavity "C", retractor 310 is cut distal of barbs 314 formed on proximal end 310a thereof. In one embodiment, this may be accomplished either within body cavity "C" or external thereof, depending on the location of needle 312. Pledget 313 may then be retrieved from body cavity "C". Alternatively, pledget 313 may remain in body cavity "C".

Figure 14:
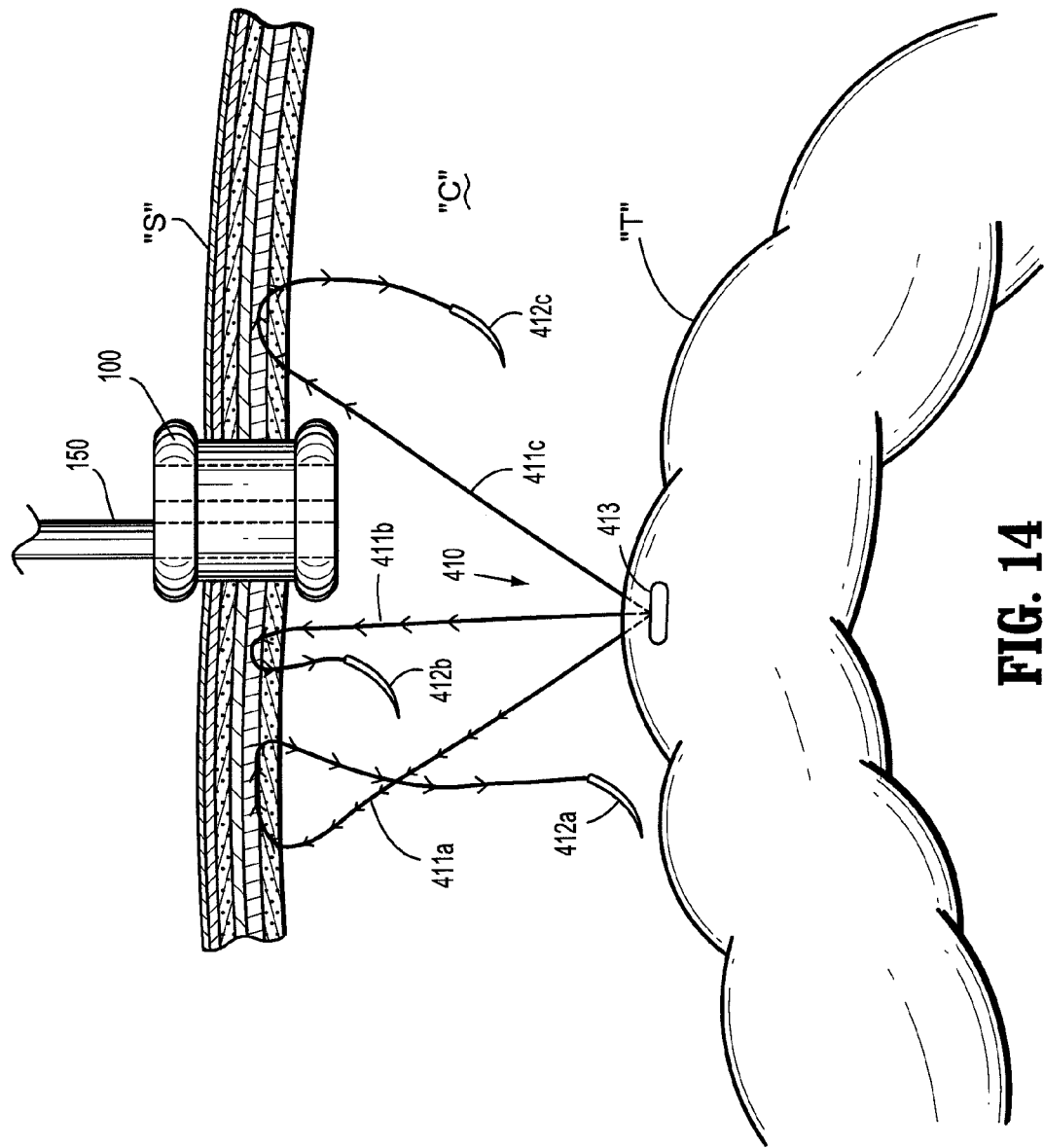
FIG. 14 illustrates yet another method of retracting tissue using still yet another tissue retractor according to the present disclosure.

Turning to FIG. 14, an alternative method of retracting tissue "T" using an alternative embodiment of the present disclosure is illustrated. A retractor 410 includes multiple body portions 411a, 411b, 411c extending from a pledget 413. Each of body portions 411a, 411b, 411c include a needle 412a, 412b, 412c, respectively. Each of body portions 411a, 411b, 411c may also include barbs 414a, 414b, 414c. Retractor 410 may be used to retract tissue "T" in substantially the same manner as any of the methods described hereinabove, further including the step of directing second and third needles 412b, 412c of body portions 411b, 411c, respectively, through tissue "T" and securing second and third body portions 412b, 412c to skin "S".

Figure 15:
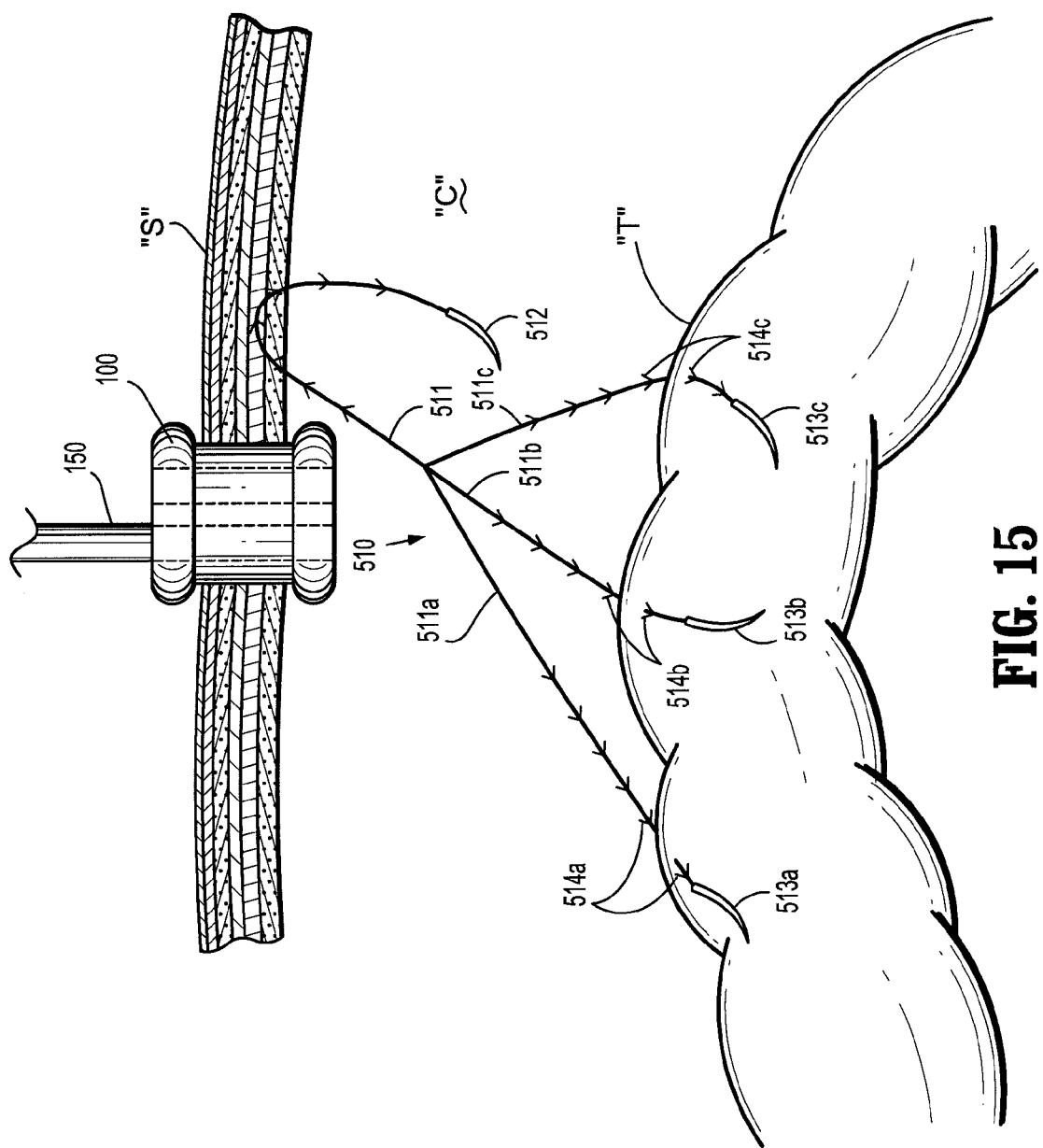
FIG. 15 illustrates still yet another method of retracting tissue using still yet another tissue retractor according to the present disclosure.

With reference now to FIG. 15, another method of retracting tissue "T" using an alternative embodiment of the present disclosure is illustrated. A retractor 510 includes multiple body portions 511a, 511b, 511c formed on a first end and a single needle 512 formed on a second end. Each of body portions 511a, 511b, 511c include a needle 513a, 513b, 513c, respectively, for directing respective body portions 511a, 511b, 511c through tissue "T". Barbs 514a, 514b, 514c are formed along body portions 511a, 511b, 511c and are configured to engage tissue "T". Barbs 514 are formed along body portion 511 to engage skin "S".

Figure 16:
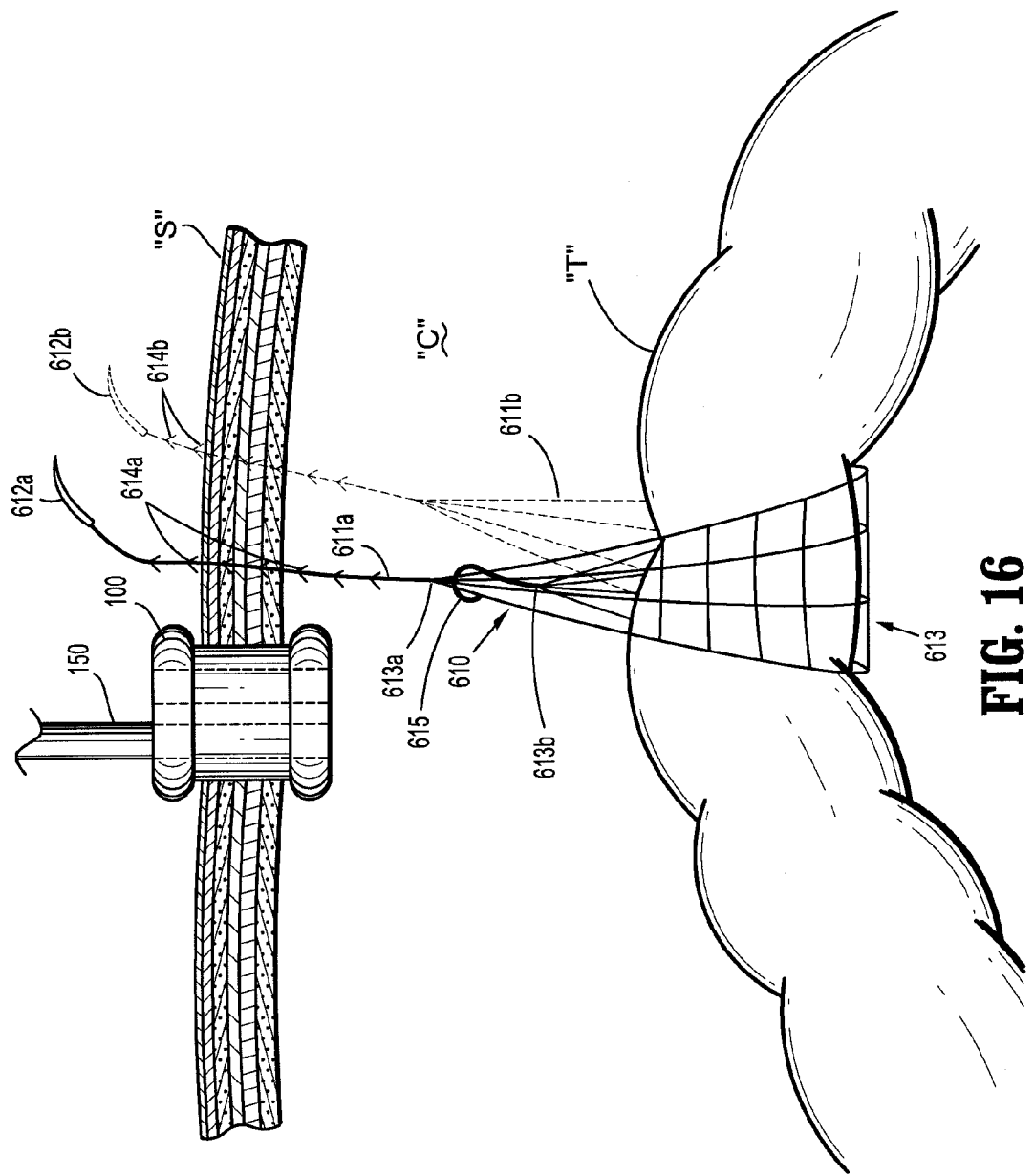
FIG. 16 illustrates still yet another method of retracting tissue using still yet another tissue retractor according to the present disclosure.

Referring to FIG. 16, yet another method of retracting tissue "T" using another embodiment of the present disclosure is illustrated. A retractor 610 includes a sling or other suspension device 613 configured to support tissue "T". Sling 613 may be formed of mesh or other support material to suspend tissue "T" in a hammock-like fashion. Sling 613 includes a first end 613a operatively connected to body portion 611a and a second end 613b including a hook, clip or other fixation means 615 for securing second end 613b of sling 613 to body portion 611a. In this manner, sling 613 may be selectively received around tissue "T". A proximal end of body portion 611a includes a needle 612a and may include barbs 614a for securing body portion 611a to or through skin "S". Alternatively, and as shown in phantom, retractor 613 may include a second end 613b operatively connected to a second body portion 611b. Second body portion 611b includes a second needle 612b and may include barbs 614b for securing second body portion 611b to or through skin "S".

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A method of retracting tissue, comprising:
providing access to a body cavity of a patient through at least one port;
providing a retractor including an elongated body portion having at least one barb formed thereon, a needle formed on a proximal end of the elongated body portion and an anchor means formed on a distal end of the elongated body portion, wherein the anchor means comprises at least one pledget;
directing the needle of the retractor through a section of tissue to be retracted;
drawing the retractor though the section of tissue until the anchor means engages the section of tissue;
directing the needle of the retractor through skin of the patient;
pulling the needle of the retractor to temporarily retract the section of tissue and to engage the at least one barb of the elongated body portion with the skin of the patient to maintain the section of tissue in a retracted configuration; and
cutting the retractor at a location on the elongated portion to release the section of tissue from the retracted configuration; and
removing the retractor from the body cavity of the patient.

2. The method of claim 1, wherein the retractor is completely received within the body cavity.

3. The method of claim 1, wherein directing the needle of the retractor through the skin comprises directing the needle through a wall of the body cavity.

4. The method of claim 1, wherein the elongated body portion of the retractor includes multiple body portions.

5. The method of claim 1, wherein the elongated body portion of the retractor includes multiple needles.

6. The method of claim 1, wherein the at least one barb includes distally extending barbs.

7. The method of claim 1, further including manipulating a portion of the retractor to manipulate the section of tissue.

* * * * *